United States Patent [19]

Hedlund et al.

[11] Patent Number: 4,863,964

[45] Date of Patent: Sep. 5, 1989

[54] METHOD FOR THE STABILIZATION OF DEFEROXAMINE TO CHELATE FREE IONS IN PHYSIOLOGICAL FLUID

[75] Inventors: Bo E. Hedlund, New Brighton; Philip E. Hallaway; Samuel S. Panter, both of Minneapolis; John W. Eaton, Minneapolis, all of Minn.

[73] Assignee: Biomedical Frontiers, Inc., Minneapolis, Minn.

[21] Appl. No.: 87,631

[22] Filed: Aug. 20, 1987

Related U.S. Application Data

[63] Continuation-in-part of Ser. No. 751,069, Jul. 2, 1985, abandoned.

[51] Int. Cl.$^4$ ................. A61K 31/715; A61K 31/185
[52] U.S. Cl. ...................................... 514/575; 514/54; 514/59; 514/60
[58] Field of Search ............... 514/575, 836, 970, 776, 514/778, 777, 781, 54, 60, 59; 424/484, 485, 488

[56] References Cited

U.S. PATENT DOCUMENTS

| | | | |
|---|---|---|---|
| 3,158,552 | 11/1964 | Gaeumann et al. | 435/128 |
| 3,957,435 | 5/1976 | Adams et al. | 424/85 |
| 3,961,038 | 6/1976 | Benes | 424/1 |
| 4,024,073 | 5/1977 | Shimizu et al. | 536/55.1 |
| 4,397,867 | 8/1983 | Blake | 514/575 |
| 4,425,319 | 1/1984 | Yokoyama et al. | 424/1.1 |
| 4,613,616 | 9/1986 | Winston et al. | 514/836 |

FOREIGN PATENT DOCUMENTS

087786 9/1983 European Pat. Off. .

OTHER PUBLICATIONS

Gutteridge et al., cited in Chem Abstracts, vol. 92:141457r.
Dawson et al., in Development of Iron Chelators for Clinical Use, Martell et al (eds), Elsevier Press, (1981), pp. 201-209.
Ramirez et al., J. Macromol. Sci.-Chem., A7(5), pp. 1035-1045, 1973.
Ramirez et al., J. Macromol. Sci.-Chem., A10(1 & 2), pp. 309-365, 1976.
Tam et al., PNAS USA, vol. 73, No. 6, pp. 2128-2131, 1976.
Hershko et al., Brit. J. Hematol., 51, pp. 251-260, 1982.
Paller et al., J. Clin. Invest., vol. 74, pp. 1156-1164, 1984.
Modell et al., The Clinical Approach to Thalassaemia, 1984.
Leung et al., Clin. Chem., vol. 35, No. 1, pp. 20-23, 1985.
Vercellotti et al., J. Clin. Invest., vol. 76, pp. 956-962, 1985.
Till et al., J. Free Radicals in Biol. and Med., vol. 1, pp. 163-168, 1985.
Woodson et al., abstract, Clin. Res., vol. 34, No. 2, p. 678A, 1986.
Fleischer et al., Stroke, vol. 18, No. 1, pp. 124-127, 1987.
Braughler et al., J. Biol. Chem., vol. 262, No. 2, pp. 10438-10440.

*Primary Examiner*—Ronald W. Griffin
*Assistant Examiner*—Jacqueline M. Stone
*Attorney, Agent, or Firm*—Merchant & Gould

[57] ABSTRACT

A method for scavenging free iron or aluminum in fluids such as physiological fluids involves a provision in such fluids of a soluble polymer substrate having chelator immobilized thereon. According to the invention preferred such compounds comprise polysaccarides or proteins having a deferoxamine moiety thereon. Such a compound can be used for the treatment of iron overload, as well as to inhibit cell damage from oxidation/reduction reactions. In one embodiment, cell damage during reperfusion is inhibited, through provision of the chelating moiety at the site of reperfusion.

7 Claims, 5 Drawing Sheets

WHOLE BLOOD CONCENTRATION OF DFO AND IMMOBILIZED DFO FOLLOWING INTRAVENOUS INJECTION

REDUCED TOXICITY OF DEX-DFO

DISTRIBUTION OF IRON BETWEEN DFO AND DEX-DFO

DFO AND DEX-DFO INHIBIT LIPID PEROXIDATION EQUALLY WELL

INHIBITION OF Hb MEDIATED TBARS FORMATION

PMN LYSIS OF ERYTHROCYTES AFTER I HOUR

RETENTION OF DEXTRAN AND DEXTRAN-DFO

METHOD FOR THE STABILIZATION OF DEFEROXAMINE TO CHELATE FREE IONS IN PHYSIOLOGICAL FLUID

RELATED APPLICATION

The present application is a continuation-in-part application of U.S. patent application Ser. No. 751,069 filed July 2, 1985 now abandoned.

BACKGROUND OF THE INVENTION

Deferoxamine deferrioxamine or desferrioxamine) and its pharmaceutically-acceptable salts are chelating agents which exhibit high binding affinities for metal ions such as aluminum and ferric ions. Deferoxamine mesylate is commercially available and has been used to treat severe iron intoxication, iron storage disease or iron overload resulting from hemolysis due to drugs, thalassemia, sickle-cell anemia, frequent blood transfusions and the like. McLachian (U.S. Pat. No. 4,419,365) discloses the treatment of Alzheimer's disease by the administration of deferoxamine salts to increase aluminum excretion. Aluminum dialysis encephalopathy can also be reversed by treatment with deferoxamine, R. S. Arze et al., Lancet ii, 1116 (1981).

There are a number of problems with the clinical use of deferoxamine mesylate. Since the drug is not appreciably absorbed when orally administered, it generally must be given parenterally. Once administered, the drug is very rapidly excreted. For example, in humans the drug exhibits a half-life of only about 5–10 min. Chelation therapy with the drug, as a result, involves continuous infusion or frequent intramuscular injections, which may cause pain and/or induration at the injection site. Further, the acute and chronic toxicity of deferoxamine is relatively high, making the substance less versatile for therapeutic uses.

A need exists for an agent, useful in iron chelation therapy, that is resistant to in vitro or in vivo degradation and/or excretion. A further need exists for a method to prolong the effective lifetime of deferoxamine following in vivo administration. Also, a preferred deferoxamine agent having reduced toxicity is needed.

The substance deferoxamine is often abbreviated DFO or DES (not to be confused with diethylstilbesterol). For consistancy, only the abbreviation DFO will be used herein. Terms such as "Dextran-DFO" mean an adduct of the polymer (dextran) with DFO. Such an adduct may include more than one DFO moiety per unit substrate.

SUMMARY OF THE INVENTION

The present invention is directed to a method for reducing the concentration of free ferric or aluminum ions in a physiological fluid by chelating the metal ions with a stabilized form of deferoxamine. In preferred applications of the present invention the deferoxamine is stabilized in a manner which reduces its toxicity and increases its in vivo vascular retention time.

The deferoxamine is stabilized by covalent bonding to a pharmaceutically-acceptable polymer so that the deferoxamine substantially retains its ability to complex ferric and aluminum ions. For in vivo use, e.g. in the blood stream, the deferoxamine is preferably bound to a water-soluble biopolymer such as a polysaccharide or a protein. When intended for the in vitro complexation of ferric ion, e.g from an extracorporeal stream of blood, deferoxamine may sometimes be bound to a biologically-inert, water-insoluble polymeric support such as cellulose, agarose or a cross-linked dextran.

Soluble polymer : deferoxamine complexes display an number of useful and unexpected characteristics. The rate of clearance from the blood of test animals of a chelating agent comprising deferoxamine bound to a water-soluble polymer is greatly retarded when compared with the clearance of non-immobilized deferoxamine mesylate. This increased vascular retention of the chelating (deferoxamine) moiety may result in increased efficacy. Also, the toxicity of deferoxamine is substantially reduced when the deferoxamine is introduced as a chelator according to the present method. Further, polymer : deferoxamine may, under certain circumstances, be more efficient in mediating excretion of (isotopic) iron from iron-overloaded animals. Therefore, the present invention provides a method for the in vivo stabilization of deferoxamine with advantageous results.

The present invention also concerns inhibition of cell damage from oxidation/reduction reactions by providing at a selected site, an immobilized chelator. The chelator will scavenge free iron, inhibiting catalytic action. A preferred application of this latter method is in protection of/tissue during reperfusion.

DETAILED DESCRIPTION OF THE INVENTION

Figure 1:
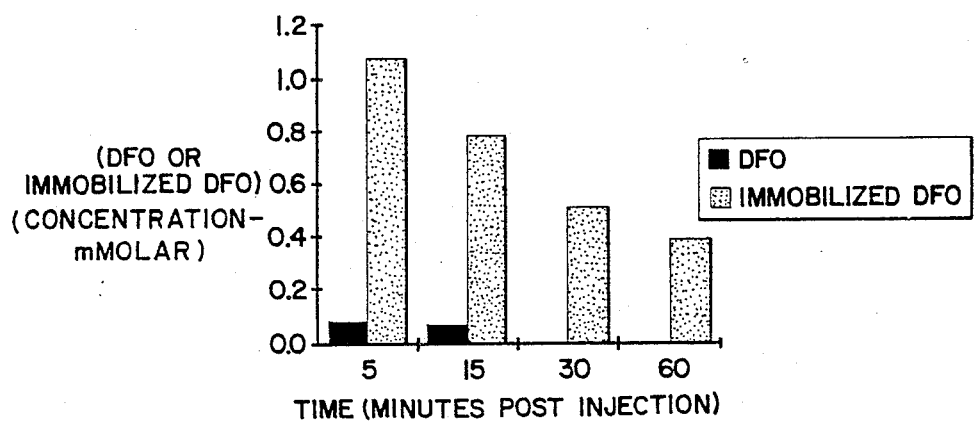
FIG. 1 is a graph showing the results of an experiment comparing the in vivo clearance of deferoxamine and an immobilized deferoxamine.

The chelating agents employed in the present invention are prepared by covalently bonding deferoxamine to a pharmaceutically-acceptable organic polymer. Methods for the preparation of deferoxamine (N-[5-[3[(5aminopentyl)hydroxycarbamoyl]propionamido]-pentyl]-3-[[5- (N-hydroxyacetamido)pentyl]-carobamoyl]propionohydroxamic acid) and its pharmaceutically-acceptable salts have been disclosed, e.g. by Prelog et al., in *Helv. Chim. Acta,* 45, 631 (1962); Bickel ]et al., *Helv. Chim. Acta,* 46 1385 (1963); in German Pat. Spec. 1,186,076 and in U.S. Pat. No. 4,419,365, the disclosures of which are incorporated by reference herein. Such salts include the acid addition salts of methane sulfonic acid, phosphoric acid, acetic acid lactic acid, tartaric acid, citric acid and the like.

Preferably, formation of chelating agents according to the present method involve an anchoring of the deferoxamine moiety to the substrate biopolymer in such a manner that:

1. the chelating ability, in vitro, of the deferoxamine moiety remains substantial, preferably on the order of non-anchored deferoxamine:
2. the toxicity of the deferoxamine moiety is substantially reduced and
3. the vascular retention time for the anchored deferoxamine moiety is substantially increased relative to non-anchored deferoxamine.

It is preferred to bind the terminal amino (NH$_2$) group of deferoxamine to a molecule of a pharmaceutically-acceptable organic polymer. The amino group may be bonded directly to a carboxy-acid moiety on the polymer, e.g. to form an amide linkage. Preferably, the deferoxamine amino group will be directly bonded to an aldehyde (CHO) moiety on the polymer via the reaction sequence:

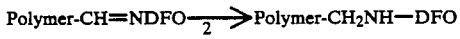

wherein reaction 1 yields a Schiff base which is reduced in reaction 2 to yield a covalent linkage. It is noted that more than one deferoxamine moiety may be bound to a single substrate (polymer) molecule Application of the above process, wherein the polymer is a soluble biopolymer such as a polysaccharide or a protein, leads to a soluble chelating agent possessing the desired characteristics outlined above. That is, the resulting chelating agent is very effective in chelating ability. Further, the bound chelating agent exhibits substantial advantages, primarily relating to diminished toxicity, mediation of in vivo iron excretion, and increased vascular retention time. It will be understood from the below reported experimental results that behavior of the bound chelating agent is not always readily predictable from data concerning the non-bound or non-immobilized chelator.

Aldehydic groups can be introduced into the polymer substrates by known techniques, e.g. by the oxidation of carbohydrates or other diols to dialdehydes with sodium metaperiodate. See, for example, M.B. Wilson, et al. in *Immunofluorescence and Related Staining Techniques,* W. Knapp et al., eds., Elsevier/North Holland Biomedical Press (1978) at page 215', Flemming et al., *Acta Biol. Med. Ger.,* 30, 177 (1973); and, S.-C. Tam et al., in *P.N.A.S. USA,* 73, 2128 (1976), the disclosures of which are incorporated by reference herein.

In some applications, the terminal amino group on deferoxamine can also be bonded to an amino group on the polymer indirectly, by the use of a dialdehyde linking agent such as gluteraldehyde, followed by reduction, e.g., with sodium borohydride.

The mole ratios of deferoxamine/polymer attainable by these reactions will vary widely, depending on factors such as the number of reactive groups on the polymer, steric hindrance, rate and extent of Schiff base or amide formation, and the like. As an example, about 0.6–0.7 g of deferoxamine can be bonded to about 2.5 g of reacted Dextran 40, via reaction of the deferoxamine with aldehyde groups introduced into the dextran, followed by reduction.

Organic polymers used as substrate material for reaction with deferoxamine may be either watersoluble or water-insoluble. Chelating agents formed from either will have utility in various applications, provided the polymer and chelating agent are pharmaceutically- and/or otherwise compatible with the physiological solutions with which they will have contact during use.

However, preferred preparation of chelating agents for use in vivo provides special problems and requires special characteristics. The chelating agent must be sufficiently soluble for ease of introduction. The chelating moiety of the agent must remain effective as a chelator, even in vivo. The agent should show improved vascular retention and be efficacious in generating iron excretion from animals. The agent should not be substantially toxic, at least at or near therapeutic levels, and preferably within about 5 to 10 times therapeutic levels. The polymeric substrate should not cause significant side reactions, and thus should be selected from polymers which are biocompatible.

It has been found that polymers apparently useful for application according to an in vivo application of the present invention include polysaccharides such as the dextrans and hyaluronic acid, starch derivatives, and proteins such as human serum albumin, plasma protein fraction (human) and the like. Polymer starting materials such as the dextrans human albumin and plama protein fraction are commercially available as water-soluble preparations or as solutions. See *Remington's Pharmaceutical Sciences,* A. Osol., ed., Mack Publishing (16th ed. 1980) at pages 759–76.

Chelating agents intended for use to reduce ferric and/or aluminum ion concentrations in a physiological fluid, in vivo, are preferably administered, as solutions, parenterally, e.g. by intramuscularoor intravenous injection or infusion, or via buccal, rectal or vaginal routes. The appropriate dose will be adjusted in accord with appropriate clinical factors including: the pathology to be treated; the patient's age, size and weight; the mode of administration; binding capacity of the chelator, and the like. For example, see B. Modell et al., in *The Clinical Approach to Thalassaemia,* Grone and Stratton, New York (1984) at chapter 13.

Bound chelating agents based on water-insoluble, pharmaceutically-acceptable polymeric substrates, may be employed in vivo, e.g. in the form of implants or as circulating beads or vesicles, for the long-term reduction of ferric or aluminum ion levels. However, these agents are preferably employed for the removal of ferric or aluminum ions from an extracorporeal stream of a physiological fluid. For example, a stream of blood from a suitable reservoir or as drawn directly from a patient can be brought into contact with a solid support comprising deferoxamine which has been bound to the insoluble biologically inert polymer. The support can take the form of a membrane, filter, beads, microporous tubes and the like. Following a contact time sufficient to lower the target metal ion concentration to the desired level, the blood can be returned to the patient.

It will be understood that provision of a water-insoluble chelating agent poses, in many ways, a substantially simpler problem than provision of a watersoluble agent for in vivo use. For example, stability, toxicity and vascular retention time are generally not a problem for insoluble systems.

A wide variety of insoluble synthetic and natural organic polymers can be bound to deferoxamine by the techniques described hereinabove, including water-insoluble agaroses (Sepharose ®), cross-linked dextrans (Sephadex ®), cellulosics (e.g., paper and cotton), starches and the like.

Although the invention has been described herein primarily with respect to the use of the present chelating agents to reduce the ferric or aluminum ion concentration in blood, the methods of the present invention are applicable to wide variety of fluids including a wide variety of aqueous physiological fluids, wherein the chelating agent can operate to complex iron or aluminum. Such fluids include the various mammalian fluids such as blood, lymph, cerebrospinal fluid, semen and the like. Furthermore, within the context of the present invention and disclosure, the terms "physiological fluid" or "physiological solution", or variants thereof, include within their meaning aqueous biocompatible solutions such as blood or plasma substitutes, intravenous solutions such as physiological salt solutions, nutrient solutions and the like.

It will also be understood that in some applications, compounds according to the present invention may be used to deliver a metal to a desired location.

The invention, its application and its scope and utility are further understood by reference to the following detailed discussions of examples and experiments.

EXAMPLE 1

Immobilization of Deferoxamine on Dextran

Two experiments showing immobilization of deferoxamine (DFO) on dextran were conducted as follows:

a. Solid sodium metaperiodate was added to a stirred, 10% solution of Dextran 40 (Rheomacrodex ®, Pharmacia, Uppsala, Sweden) (average molecular weight 40,000) in normal saline (500 ml to a final concentration of 0.28 M NaIO$_4$. The solution was stored at 4° C. for 18 hours. Solid sodium bisulfite was added to the solution with stirring until it became clear. The reaction mixture was then dialysed for 12 hours against distilled water to remove impurities. The resultant dialdehyde-containing dextran material had a final concentration of 5% in distilled water.

The mesylate of deferoxamine (Desferal ®, Ciba-Geigy, Summit, NJ) (3.3 g) was added to 50 ml of a 5% solution of the activated dextran which had been buffered with 5 ml of 1 M sodium cacodylate buffer, pH 6.0. The reducing agent sodium cyanoborohydride was simultaneously added with the Desferal ® to continuously reduce the Schiff base. The final concentration of sodium cyanoborohydride was 20 mM. The reaction mixture was allowed to stand at 4° C. for 18 hours, then sodium borohydride was added to a concentration of 40 mM to reduce any unreacted aldehyde groups. After 2 hours at 20° C., the reaction mixture was dialysed for 18 hours against distilled water to remove buffer ions and unreacted reducing agents, affording about 100 ml of an aqueous solution which contained about 6–0.7 g of deferoxamine covalently bound through the primary amino group to 2.5 g of dextran (20% yield, ca. 16 moles of deferoxamine/mole of dextran, m. w. 40,000).

b. Rheomacrodex ™ was again used as the dextran material. The dextran was initially oxidized with sodium metaperiodate to yield aldehyde groups, as above, to which the amino group of deferoxamine (DFO) was subsequently to be covalently attached. For this purpose solid sodium periodate was dissolved in 500 ml of a 10% aqueous solution of dextran to a final concentration of about 0.3 M. This solution was stored at 4° C. for 18 hours. The solution was then titrated with 0.6 M sodium bisulfite to initially yield a dark brown color, followed by a yellow solution which became clear upon the addition of further bisulfite. The resulting solution was dialyzed extentively against distilled water and the dialysate was then lyophilized. The freeze dried material represents a polyaldehyde derivative of dextran and is referred to herein as "activated" dextran. Approximately 40 grams of activated dextran is typically obtained at this point.

To covalently attach deferoxamine to the activated dextran, about 10 g of the activated dextran were dissolved in 100 ml of distilled water. Activated dextran material is less soluble than normal dextran and the resulting solution is initially very viscous and opaque. Therefore, the activated dextran was added stepwise to the solution. With time, the entire 10 g of activated dextran did go into solution. Extended stirring reduced viscosity.

Solid DFO was added to give a final concentration of 0.1 M (6.55 g). At this point, 630 mg of sodium cyanoborohydride were added to yield a final concentration of 0.1 M.

The stirring was continued for another two hours at room temperature, at which point a second reduction step was initiated by the addition of 0.5 grams of sodium borohydride. The entire mixture was allowed to stir for another two hours, at which point dialysis was initiated. The dialysis was continued for several days, using five or six changes of the 15 liter dialysis vessel. Following completion of dialysis the dextran-deferoxamine (dextran-DFO) adduct was lyophilized. A total of 8.7 grams of slightly yellowish, flaky, material was obtained.

The dextran-DFO (DEX-DFO) adduct was characterized in terms of deferoxamine content by making a 100 mg/ml stock solution in normal saline. A fifty-fold dilution of this stock solution with 1.0 mM ferrous sulfate gave an absorbance value of 1.703 at 429 nm, following overnight incubation to ensure full completion of the reaction between chelator and iron. Therefore, the deferoxamine concentration on the stock was 37.0 mM. (The millimolar extinction coefficient of ferrioxamine (DFO-iron complex) is (2.3 cm$^{-1}$). Since the molecular weight of the incorporated DFO can be considered to be 560 (the methane sulfonate anion being lost) the solid material contained about 20.7 mg of DFO per 100 mg material, the remainder being dextran carrier.

The dextran-deferoxamine adduct was soluble in saline up to 200 mg/ml, yielding a rather viscous, slightly yellow solution. The total recovery of deferoxamine in the 8.7 g of final product was 1.80 g. The initially added DFO (6.56 ) contains 5.6 g of chelating agent (the remainder being anion). Therefore, 32% of the deferoxamine chelating agent was incorporated into the polymeric adduct.

EXAMPLE 2

Immobilization of Deferoxamine on Hyaluronic Acid

Hyaluronic acid (HA) was obtained from Diagnostic, Inc., Minneapolis, MN. A sample of 1.0 gram of sodium hyaluronate (Lot No. VI 1686) was used. The material had been alcohol precipitated and dried.

For periodate oxidation, 400 mg of HA were dissloved in 20 ml distilled water. Based on published studies [Scott, J.E. and Harbinson, R. J. incorporated herein by (1968), *Histochemic*, 14, 215–200], reference, the oxidation was carried out in the presence of 0.2 M sodium perchlorate. The HA stock solution was reacted with 20 mM sodium metaperiodate in the presence of 0.2 M sodium perchlorate. The material was stored at 4° C. for 18 hours. The unreacted periodate was then titrated with 0.04 M bisulfite When the last yellow color had disappeared the activated HA was extensively dialysed against distilled water. The activated HA was then lyophilized.

Lyophilized activated HA (150 mg) was dissolved in 3.0 ml of normal saline (0.15 M NaCl). Covalent attachment of deferoxamine was initiated by adding the chelator to a concentration of 100 mM (197 mg) and allowing the mixture to react overnight at room temperature. The following day, 18.8 mg of sodium cyanoborohydride were added. This was allowed to react for another 24 hours, at which time 10 mg sodium borohydride were added. After the bubbling had ceased (3 hrs.) the reaction mixture was extensively dialysed against distilled water. Following the dialysis, the HA-DFO adduct was lyophilized. The yield was 180 mg of solid material.

To determine the deferoxamine content of the (HA-deferoxamine) derivative, 50 mg were dissolved in 1.0 ml saline. A 100 ml aliquot was added to 3.0 ml of 1.0 mM ferrous sulfate and the color was allowed to develop overnight. An optical density of 1.800 was obtained for this preparation. This indicates that the concentration of deferoxamine [.n the stock solution was 24.3 mM. This value corresponds to a weight per volume concentration in the stock or 13.6 mg/ml. Since the actual concentration of the stock was 50 mg/ml it follows that approximately 27% of the solid material represents the covalently bound deferoxamine. Since 180 mg of solid material was obtained and 27.2% of this represents bound deferoxamine, one can conclude that approximately 25% of the 197 mg of deferoxamine used was recovered in the polymeric material.

EXAMPLE 3

Immobilization of Deferoxamine on Hydroxyethyl Starch

The starting material for this procedure was clinical grade hydroxyethyl starch (Hespan TM, American Critical Care). For periodate oxidation 100 ml of a 6% solution of hydroxyethyl starch (HES) was withdrawn and solid sodium meta-periodate was added to 100 mM. The material was allowed to react for 18 hours at 25° C. The following day the unreacted periodate was titrated with 132 ml of 200 mM sodium bisulfite. When the solution was clear, the activated HES was extensively dialysed against distilled water. The dialysed HES (50 ml), which at this point had a concentration of 20 mg/ml, was reacted with deteroxamine. The chelator was dissolved in the HES solution to a final concentration of 50 mM (1.65 grams). Sodium cyanoborohydride (157 mg) was added -after one-half hour and sodium borohydride (95 mg) was added the following day. Following cessation of bubbling, extensive dialysis was initiated. The dialysed material was lyophilized, and 0.97 g of said material were obtained. The recovered material was fully soluble in saline and a 20 mg/ml stock solution was prepared. A sixteen-fold dilution of this material with 1 mM ferrous sulfate had an absorbance of 1.132 at 429 nm, flowing overnight incubation. The concentration of deferoxamine in the stock was calculated at 7.9 mM or 4.4 mg/ml. This indicates that 22% by water of the HES-deferoxamine (HES-DFO) adduct was deferoxamine.

EXAMPLE 4

Immobilization of Deferoxamine on Methyl-Cellulose

The methyl ether of cellulose was obtained from Dow Chemical Co., Midland, MI. The manufacturer refers to the polymer as "EXPERIMENTAL POLYMER XD 8928.00." The material had the trade name METHOCEL TM. A 500 g container of cellulose ether, lot MM841002221X, was used as the source of material.

The solubility of methyl cellulose in water is limited. Solutions of the XD polymer at concentrations above 3% tend to be highly viscous. The activation was carried out in the following manner.

A 3% solution of XD polymer was prepared by dissolving 3.0 grams of the polymer in 100 ml distilled water. The material was allowed to stir overnight. The volume decreased to 90 ml due to evaporation. At this point 1.92 g of sodium periodate were added to reach a concentration of periodate of 100 mM. Stirring was continued overnight. The stirred material was titrated with 100 mM bisulfite. During the titration procedure a heavy brown precipitate was formed. After addition of 200 ml of 100 mM bisulfite a mixture of white and brown amorphous precipitate was observed in a clear solution. Following extensive stirring 48 hrs) all of the precipitate eventually dissolved. Extensive dialysis was initiated at this time. The product was lyophilized and is referred to herein as "activated" XD.

A portion of a 10 mg/ml- aqueous solution of activated XD was treated with 100 mM deferoxamine (1.31 g in 20 ml). After the deferoxamine had been dissolved, solid sodium cyanoborohydride was added to a concentration of 100 mM (126 mg). The material was allowed to react overnight, at which point solid sodium borohydride (76 mg) was added to a concentration of 100 mM. Extensive dialysis was initiated as soon as bubbling from the borohydride had ceased. The material, referred to as XD-DFO, was lyophilized following several days of dialysis against distilled water with 5-6 changes of the 15 liter carboy.

To determine the degree of incorporation of deferoxamine in XD-DFO, a 50 mg/ml stock solution was made from the lyophilized preparation in normal saline. The stock solution was then diluted 31-fold with freshly prepared ferrous sulfate (1.0 mM in saline) and the optical density was read at 429 nm after an extended incubation period. The final absorbance value was 1.521, indicating that the concentration of deferoxamine in the XD-DFO stock was 20.5 nM. The weight content of deferoxamine in this material was therefore 11.5 mg/ml, corresponding to 23.0% of the weight of the polymeric chelator. Since a 50 mg/ml solution of methyl cellulose corresponds to a 280 mM solution of the methylated hexose subunit (approx. mol. weight 108) the derivatized polymer had one DFO molecule for each 13-17 methylhexose subunits. This was approximately the same degree of incorporation as obtained for the dextran derivative of deferoxamine.

EXAMPLE 5

Immobilization of Deferoxamine on Inulin

Two forms of inulin were obtained from Sigma Chemical Co. One was prepared from chicory root (I-2255) and the other from dahlia tubers (I-3754). Solutions of both forms of inulin indicated that the chicory root material was somewhat more soluble than the other. Therefore, the chicory root material was selected as the substrate.

Periodate activation was carried out using 5.0 grams of I-2255 material dissolved in distilled water. It was noted that moderate heating to 60-70° C. markedly improved solubility of the inulin. The concentration of inulin during overnight oxidation with 100 mM periodate was 5%. The unreacted periodate was reduced by 200 mM sodium bisulfite. The 100 m of the I-2255 solution required 129 ml of the bisulfite before the final yellow color disappeared. The activated inulin was then dialysed against distilled water using dialysis tubing with low molecular weight cutoff. Following three changes of dialysate, 350 ml of dilute activated inulin was obtained. The solution contained some solid material and was therefore centrifuged. The clear supernatant was retained and a fraction of the activated inulin solution was lyophilized.

For preparation of the inulin-deferoxamine complex, 1.0 g of activated inulin (I-2255) was dissolved in 50 ml normal saline under mild heating. Solid deferoxamine was added to a concentration of 50 mM (1.64 g). This solution was allowed to stir for one hour at room temperature. At this point, sodium cyanoborohydride was added to a concentration of 50 mM (0.157 g). The mixture was allowed to stir for 18 hours. Sodium borohydride was added to yield a final concentration of 50 mM (0.09g). This mixture was allowed to stir another 24 hours at which point dialysis was initiated using low molecular weight cutoff membranes. Following six changes of water over 96 hours, dialysis was terminated yeilding 90 ml of the inulin-deferoxamine derivative. This material was lyophilized to yield 0.86 g of product.

In order to determine the degree of incorporation of deferoxamine into the inulin-deferoxamine complex, a solution of the material containing 20 mg/ml was prepared. This material was freely soluble at this concentration. A small aliquot (100 ml) of this material was mixed with 3.9 ml of 1.0 mM ferrous sulfate. Following completion of the reaction an optical density of 0.656 was obtained at 429 nm. Taking into account the dilution factor and the known extinction coefficient of ferrioxamine, the concentration of deferoxamine in the stock solution was determined to be 11.4 mM. Using a molecular weight of deferoxamine of 560, the concentration of DFO in mg/ml was 6.4 mg/ml. Since the total weight of inulin-deferoxamine was 20 mg/ml in the stock, 32% of the solid material was attached chelator. Furthermore, if the molecular weight of inulin is assumed to be 5,000, the molar concentration of inulin was 4 mM in the stock, indicating that each inulin molecule contained approximately three molecules of bound chelator.

EXAMPLE 6

Immobilization of Deferoxamine on Serum Albumin

Gluteraldehyde was purchased from Sigma Chemical Co., St. Louis, Mo. (Grade I, specially purified 25% aqueous solution). The gluteraldehyde was diluted with normal saline to yield 10 ml of 100 mM stock solution. A 100 mM stock solution of deferoxamine was prepared by dissolving 656 mg of deferoxamine in 10 ml saline. The solution of gluteraldehyde was slowly added to the deferoxamine solution to yield 20 ml of a solution 50 mM in both deferoxomine and gluteraldehyde. The solution was allowed to stand at room temperature for one hour.

Bovine serum albumin (BSA, Sigma, fraction V powder, A7906, Lot 848-0099) was employed. BSA (750 mg) was allowed to dissolve directly into 7.5 ml of the solution of deferoxamine and gluteraldehyde. Sodium cyanoborohydride (40 mg) was added and the reaction mixture was gently stirred for twelve hours. Extensive dialysis was initiated (five changes over 72 hours). When dialysis was terminated some precipitated protein was observed. The material was centrifuged and the small pellet discarded. The clear supernatant was assayed for deferoxamine content. The solution of the proteindeferoxamine conjugate, which at this point had a volume of approximately 15 ml (two-fold dilution during dialysis decreased concentration from 100 to 50 mg/ml), was diluted 12-fold with 1.0 mM ferrous sulfate. This solution was allowed to stand in the cold overnight and was read against a similarly diluted albumin blank. An absorbance of 0.946 was observed at 429 nm. This indicates that the stock solution of the albumindeferoxamine adduct is 4.9 mM in deferoxamine. Since the protein concentration is aoproximately 0.75 mM there are 6.7 moles of deferoxamine per mole of protein.

EXAMPLE 7

Immobilization of Deferoxamine on Water Insoluble Substrates

The materials and chemicals used in the preparation of these deferoxamine adducts were purchased from the following supplier- Sepharose ® CL4B and Sephadex ® G-15, Pharmacia Fihe Chemicals, Piscataway, NJ; deferoxamine mesylate (Desferal ®), USP grade, CIBA Pharmaceutical Company, Summit, NJ; Whatman #1 filter paper and CF-11 cellulose powder, Whatman Limited, England; sodium cyanoborohydride and cacodylic acid, Sigma Chemical Co., St. Louis, Mo.

a. Immobilization of Deferoxamine on Sepharose ® CL4B.

One hundred ml of Sepharose ® CL4B was washed with five 100 ml aliquots of deionized water and was then resuspended in 100 ml of 200 mM sodium metaperiodate. Oxidation of the Sepharose ® was allowed to continue at room temperature for two hours with gentle mixing. The activated gel was again washed with five 100 ml aliquots of deionized water and was resuspended in 100 ml of 50 mM, pH 6.0, cacodylate buffer. Seventeen ml of 5 mM Desferal ® and 10 ml of 10 mM sodium cyanoborohydride were then added and the suspension was maintained at room temperature for 12 hours, with gentle mixing. Unreacted Desferal ® and other small molecules were removed from the Sepharose-Desferal product by washing with 0.5 liter of deionized water. Residual reactive sites were blocked by a 3.0 hour incubation with 10 mg sodium cyanoborohydride in 100 ml of 100 mM Tris buffer, pH 8.0, followed by a final wash with 0.5 liters of water. The immobilized chelator was kept as either the hydrated or dehydrated gel for future use.

The amount of immobilized deferoxamine was assayed by following the disappearance of Desferal ® in the reaction mixture supernatant. Quantitation of deferoxamine in solution is accomplished by addition of an excess amount of ferric chloride and then reading the absorbance change after 30 minutes at 430 nm using an extinction coefficient of 2.3 $mM^{-1}$. The product had 70 micromoles of deferoxamine covalently bound per milliliter of wet gel.

b. Immobilization of Deferoxamine on Filter Paper.

Whatman #1 filter paper was: cut into 20 pieces of approximately one square inch each; soaked in 100 ml 0.25 M aqueous sodium metaperiodate for 3.0 hours; and, washed with deionized water. The filter paper pieces were soaked in 100 ml of 50 mM cacodylate buffer, pH 6.0, which was also 1 mM in Desferal ®. Ten mg of sodium cyanoborohydride were then added and reduction allowed to continue for 12 hours at room temperature. The paper was washed with deionized water and then soaked with 10 mg sodium cyanoborohydride in 100 mM Tris buffer, pH 8.0. The paper was extensively washed with water and was allowed to air dry for later use. No quantitation of the amount of attached deferoxamine was done. However, the paper become bright orange when in contact with a solution of ferric and/or ferrous ions and this color could not be removed by washing. This indicates that the deferoxamine was covalently bonded to the paper rather than adsorbed.

c. Immobilization of Deferoxamine on CF-11 Cellulose Powder.

One hundred grams of dry CF-11 cellulose (Whatman) was treated with 0. 5 M aqueous sodium metaperiodate. The suspension was reacted for 18 hours at 25° C. The cellulose was extensively washed with distilled water. One hundred milliliters of wet gel was suspended in a total volume of 200 ml 0.1 M phosphate buffer (pH 6.2) in which 1.g (two millimoles) of deferoxamine had been dissolved. The concentration of deferoxamine in this solution was 10 mM. Sodium cyanoborohydride was added to the same concentration and the mixture was allowed to react for 18 hours at 25° C.

The derivatized cellulose was extensively washed in distilled water to remove excess deferoxamine, cyanoborohydride and fines. This preparation had an approximate binding capacity of 1.4 micromoles of iron per milliliter of wet cellulose. Assuming that this reflects the actual content of deferoxamine, a total of 150 micromoles of deferoxamine was bound to the 100 ml of wet cellulose. Since 2 millimoles were added initially, a 7% yield of immobilized deferoxamine was obtained.

d. Immobilization of Deferoxamine on Sephadex ® G-15.

The bonding procedure used for this matrix was as outlined above for the Sepharose ® CL4B and the CF-11 cellulose powder.

Toxicity Studies

Deferoxamine has been found to exhibit potentially troublesome toxicity, both chronic and acute. With respect to acute toxicity, overdose of deferoxamine has resulted in tachycardia and hypotension; see, for example, Whitten, C. F. et al.. "Studies in Accute Iron Poisoning. I. Desferrioxamine in the Treatment of Accute Iron Poisoning: Clinical Observations, Experimental Studies, and Theoretical Considerations", PEDIATRICS 1965, 36:322–335; Whitten, C. V. et al, "Studies in Acute Iron Poisoning: II. Further Observations on Desferrioxamine in the Treatment of Acute Experimental Iron Poisoning," PEDIATRICS 1966, 38:102–110; Westlin, W. F. et al., "Deferoxamine in the Treatment of Acute Iron Poisoning. Clinical Experience with 172 Children."CLIN. PEDIAT. 1966, 5:531–535; and Brunner, H., et al, "Wirkungen von Desferrioxaminmethansulfonate auf Kreislauf und Nierenfunktion." HELV. PHYSIOL. ACTA 1963, 21:C3–C6; the disclosures of which are incorporated herein by reference Acute toxicity of deferoxamine is observed at or near therapeutic levels. Immobilized deferoxamine according to the present invention is substantially less toxic then deferoxamine itself, as the following experiments show.

EXAMPLE 8

Toxicity of Immobilized Deferoxamine Experiment 1

Studies of acute toxicity of deferoxamine and dextran-deferoxamine adduct were carried out by intravenous (I.V.) injection in male Swiss-Webster mice. Stock solutions of deferoxamine and dextran-deferoxamine adduct were prepared in isotonic saline. A concentration of 200 mg/ml was chosen for the adduct because the viscosity at higher concentrations was unmanageable. The concentration of deferoxamine (free or immobilized) in both stock solutions was 74 mM. The percentage by weight of deferoxamine in the dextran-deferoxamine preparation was 20.7%, the remainder being the carrier polymer, dextran An aliquot of the stock solution was diluted with isotonic saline to 1.0 ml, which permitted the maintenance of a constant injection volume throughout the acute oxicity study. The mice were weighed and immobilized prior to injection. A suitable quantity of free deferoxamine or adduct was prepared in 1.0 ml isotonic saline, and was injected into the tail vein in 30 seconds or less.

Figure 2:
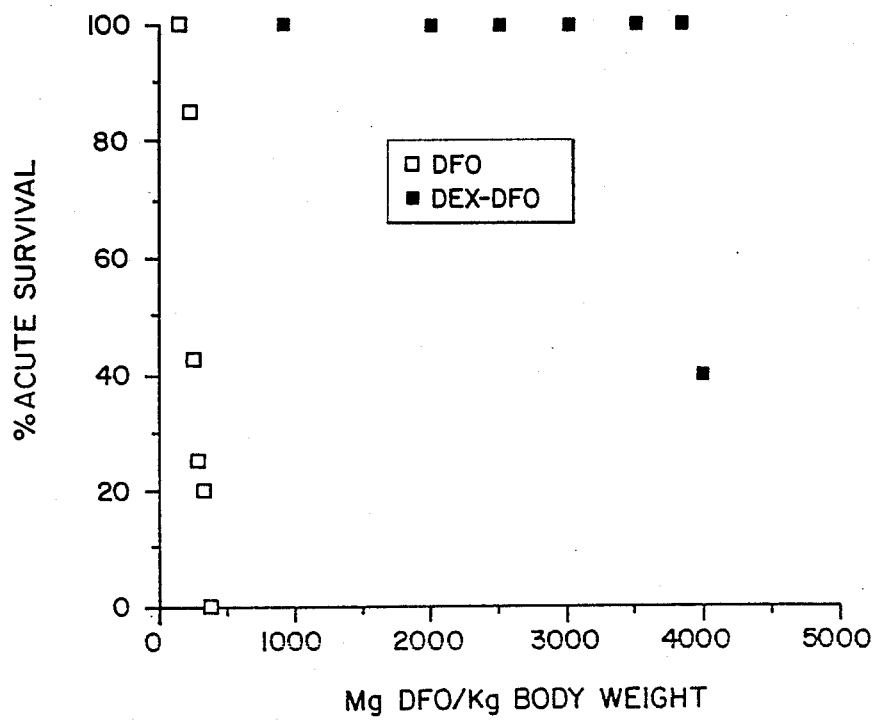
FIG. 2 is a graph showing a comparison of the toxicity of deferoxamine and an immobilized deferoxamine.

The results are outlined in FIG. 2. The acute toxicity of free deferoxamine was easily seen with an LD50 (dose producing mortality in 50% of animals) near 250 mg/kg. Animals receiving 100-250 mg/kg all exhibited labored breathing lasting for several minutes.

In the case of dextran-deferoxamine (DEX-DFO) adduct, it was found that the toxicity was surprisingly and dramatically reduced, to a point where injection of even 200 mg in a 20 g mouse was not toxic. This corresponds to 2000 mg/kg, of bound deferoxamine moiety, or nearly 10 times the lethal dose of the free drug. FIG. 2 shows that the lethal dose of deferoxamine as an adduct with dextran is between 3.5 and 4.0 g/kg or approximately 15 times that of the free drug.

Experiment 2

Studies using both inulin and hydroxyethyl starch derivatives of deferoxamine suggest that low toxicity is a general property of soluble polymeric derivatives of the chelator. The inulin-DFO adduct has been administered to mice and the results indicate that LD50 is above 2.5 g/kg, (bound chelator weight, not the total adduct weight, per kilogram body weight) although the actual LD50 level has not been established. Similarly, the hydroxyethyl starch derivative does not exhibit any apparent adverse effects at a dose of 1.0 g chelator moiety/kg body weight. Both of these polymeric forms of DFO are considerably less toxic than the free drug.

EXAMPLE 9

Vascular Retention Time of the Free Drug, Immobilized Drug, and Substrate a. In Vivo Clearance of Deferoxamine and Dextran Deferoxamine

Doses of two hundred microliters of 27.5 mM aqueous deferoxamine, or of an aqueous solution containing 3.6 mg (5.5 micromole) of the dextrandeferoxamine adduct (immobilized DFO), were injected into the tail vein of 30-40 g male Swiss-Webster mice. Whole blood was collected from etherized mice by axillary incision at 5, 15, 30 and 60 minutes postinjection. One mouse was used per time point, and 2 uninjected mice were used as controls.

For each blood sample, 50 microliters of 200 mM aqueous ferrous sulfate were added to 100 microliters of whole blood and the mixture was allowed to incubate for 5 minutes. Next, 55.0 microliters of 100% trichloroacetic acid were added. The sample was vortexed vigorously, and was then centrifuged at 1000 G for 5 minutes. Supernatant (325 microliters was removed to a microfuge tube and 150 microliters of 2 M sodium acetate was added (pH 5.5). After 18 hours at 25° C., the sample was centrifuged at 11,000 G for one minute, and the absorbance of a 425 microliter aliquot of the clarified supernatant was read at 429 nm.

Concentrations of deferoxamine or bound deferoxamine were calculated on the basis of a 2.3 cm$^{-1}$ absorptivity for a 1.0 mM solution, and the control value was subtracted prior to plotting. FIG. 1 shows the decrease in concentration of deferoxamine (DFO) and dextran-bound deferoxamine (immobilized DFO) with time. From the data summarized on FIG. 1, it can be seen that the bound (immobilized) deferoxamine was retained in the blood stream for a much longer time than was free deferoxamine.

b. Further Studies of In Vivo Vascular Retention of Polymeric Conjugates of Deferoxamine Male Swiss-Webster mice were restrained and 0.5 ml of the chelator, dissolved in saline, was injected in the tail vein. The animal was returned to the cage and following a designated time, the animal was anesthetized with ether, and blood was withdrawn by axillary incision.

i. Method for the Measurement of Free Deferoxamine in Blood

Blood from sacrificed animals was collected into heparinized tubes. Whole blood (100 to 500 microliters) was mixed with 50 microliters 200 mM ferrous sulfate (freshly prepared) and was allowed to stand for 15 minutes. Fifty five microliters of 100% trichloroacetic acid (TCA) were added, and the mixture was thoroughly mixed and centrifuged with a microfuge. Three-hundred and fifty two microliters of the supernatant was withdrawn and mixed with 150 microliters of 2.0 M sodium acetate, pH 5.5. This material was centrifuged again and the absorbance of the supernatant was measured at 429 nm against a blank prepared from blood not containing deferoxamine. The concentration of free deferoxamine in whole blood was calculated based on a molar extinction coefficient of the ferrioxamine of 2,300 at pH 5.5. This methodology can be utilized for measuring free drug in blood or plasma and also works satisfactorily for any derivative of deferoxamine that is not precipitated by TCA.

ii. Method of Measuring Polymeric Derivatives of DFO in Plasma

Blood from sacrificed animals was collected into heparinized tubes, and was centrifuged. Plasma (50 microliters) was withdrawn and mixed with 450 microliters of 10 mM sodium citrate solution containing 1 mM ferrous sulfate. The pH of the latter solution was neutral or slightly alkaline. Since most plasma samples contain some hemoglobin due to lysis during the blood collection procedure, a control tube was prepared by diluting the plasma into citrate without ferrous sulfate. Since the hemoglobin has a very high optical density at 429 nm, the tubes were read at 450 nm, which decreases the interference from hemoglobin by two thirds while reducing the ferrioxamine signal by less than 5%. The molar absorption coefficient for ferrioxamine at 450 nm has been determined to be 2,210 cm$^{-1}$. The tubes were allowed to sit overnight at 4° C to assure that all of the deferoxamine was fully reacted with the added iron. This procedure is suitable for deferoxamine concentrations in olasma of up to 5 mM. If higher concentrations of deferoxamine or deferoxamineconjugates were encountered a greater dilution of plasma into the citrate-Fe solution was required.

Figure 3:
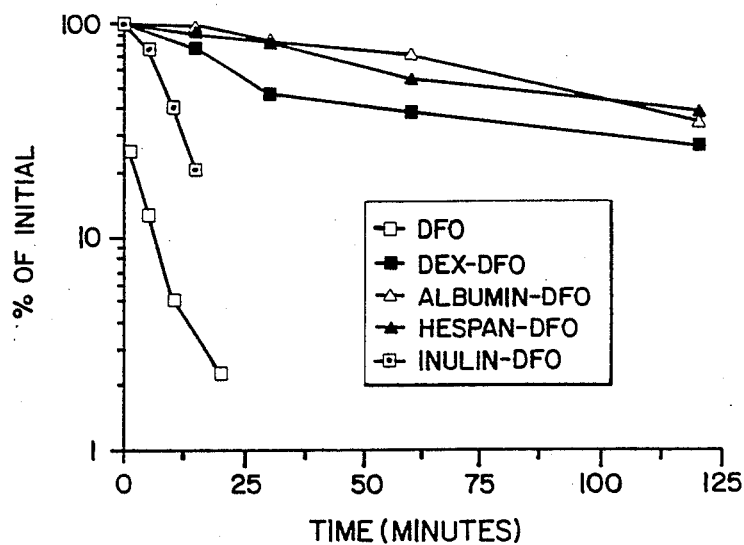
FIG. 3 is a graph showing comparison of the vascular retention times of numerous deferoxaminepolymer adducts.

In FIG. 3, the vascular retentions of four macromolecular adducts of DFO are compared to the free drug. The symbols used to illustrate the rate of disappearance of each compound are lifted in the Figure. The DFO adducts of hydroxyethyl starch (Hespan TM and serum albumin exhibited approximately the same behavior following intravenous injection. The rate of disappearance of the drug from circulation was related to the concentration measured in plasma one minute following injection. The dextran derivative had an apparent half-time of 30 minutes. The altered shapes of the curve may reflect a broader distribution of molecular weights compared to the other two polymeric forms of DFO. The small polysaccharide, inulin, with an average molecular weight of approximately 5000 Daltons, exhibited a rather low vascular half-life of 10 minutes.

c. Comparison of Rate of Clearance of Polymer-DFO Adduct to Free Polymer

Tritiated dextran was prepared by substituting tritium labeled sodium borohydride in the reduction step following periodate activation of the dextran. The tritiated dextran-deferoxamine was prepared by using tritium labeled sodium cyanoborohydride in the reduction step after introduction of the deferoxamine. In both cases the synthesis was carried out as previously described for the preparation of the dextran-deferoxamine adduct. After radiolabelling, the products were dialyzed, to remove free label, and lyophilized. The radiolabelled products were diluted at a concentration of 12.5 mg/ml in isotonic saline and the specific activities were determined by liquid scintillation counting. The tritiated dextran was diluted with 12.5 mg/ml nonradioactive dextran so that the specific activity would be the same as the dextran-deferoxamne conjugate. The final specific activity was 1.4 ×10$^7$ decays/min/ml (DPM/ml) for each solution.

Figure 10:
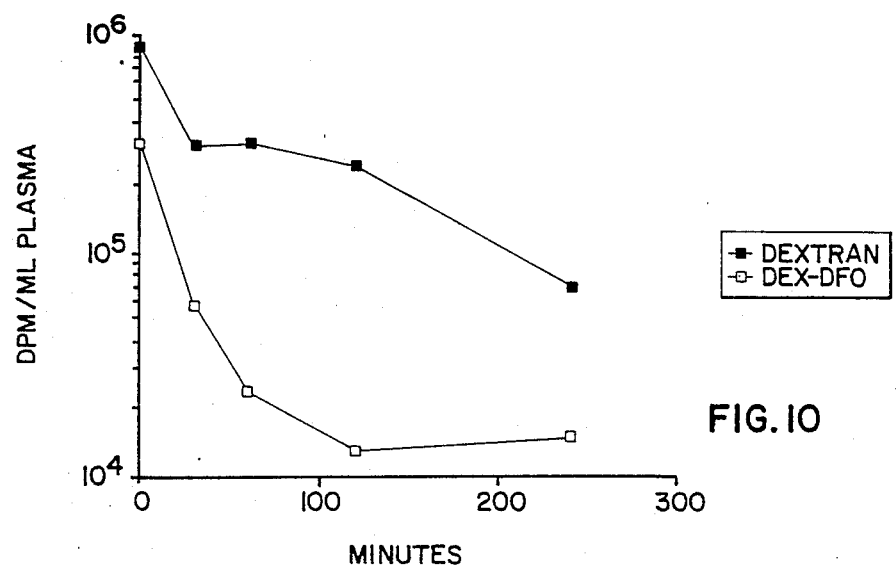
FIG. 10 is a graph showing the relative rates of clearance of dextran and a dextran-deferoxamine adduct according to the present invention.

Two hundred microliters of either dextran or dextran-deferoxamine were injected into the tail vein of 5, 30 gm., male Swiss-Webster mice. Each animal received approximately 2.5 ×10$^6$ DPM in the initial rejection. The animals were sacrificed at 0, 30, 60, 120 and 240 minutes after injection. Blood samples were collected by axillary incision, using dry heparin as an anticoagulant. The plasma was isolated by centrifugation at 1000 ×G, and a 100 microliter aliquot was counted in 15 ml of liquid scintillation fluid. All counts were corrected for quenching, and were converted to DPM/ml. A semi-log plot of plasma DPM/ml versus minutes is shown in FIG. 10.

The rate of clearance of substrate (dextran) was found to be considerably greater than that of the adduct (dextran-deferoxamine). This suggests a cooperative effect of the substrate and chelating moiety acting to keep the chelator in the bloodstream, where it will be active as a scavenger for iron or other metals.

EXAMPLE 10

Chelating Ability of the Immobilized Deferoxamine

The iron-binding characteristics of the conjugated chelator were examined by the following studies.

a. Reductive Displacement of Iron from Conjugated Ferrioxamine.

Herein, the term "ferrioxamine" is used to refer to the chelator/metal complex. The displacement of iron from ferrioxamine by gallium under reducing conditions was used as a probe for alterations in the ironbinding characteristics of the conjugated chelator. From the literature, it was determined that different siderophores release their bound iron at different rates in the presence of ascorbate and gallium, and that this is probably due to structural differences between the siderophores, see Emery, T., "Exchange of Iron by Gallium in Siderophores.", *Biochemistry*, Vol. 25, p. 4629-4633, (1986), the disclosure of which is incorporated herein by reference.

The displacement of iron from ferrioxamine was followed spectrophotometrically using ferrozine [3-(2pyridyl)-5,6-diphenyl-1,2,4-triazine-p,p'-disulphonic acid]as the indicator. Ferrozine forms a blue complex with reduced iron, which has an absorption maximum at 562 nm and a molar absorptivity of 29,000 M$^{-1}$ cm$^{-1}$. Ferrioxamine bound to 40,000 molecular weight dextran was compared to unmodified DFO as described below.

Figure 4:
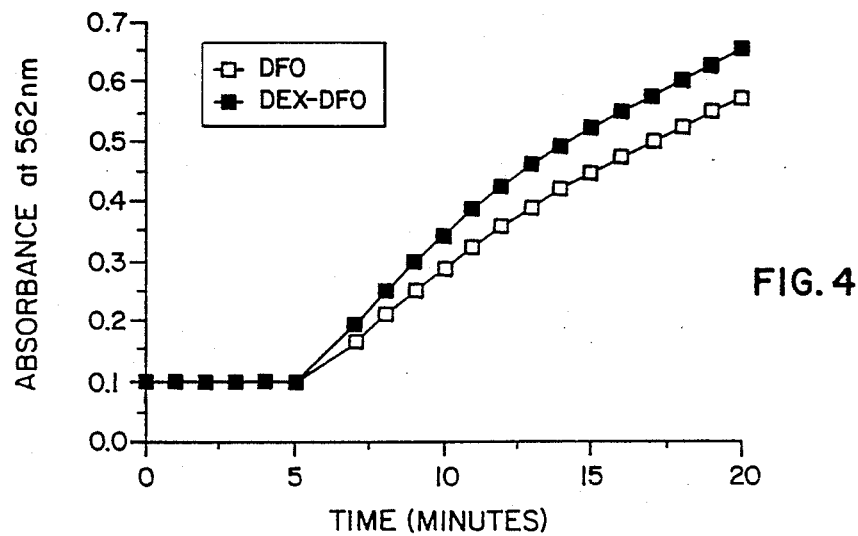
FIG. 4 is a graph showing the results of an experiment comparing chelating ability of deferoxamine and a deferoxamine-dextran addict.

Three ml of a solution of 2 mM ferrozine, 20 mM sodium ascorbate, 0.05 mM chelator, 0.05 M sodium acetate, pH 5.4, were pipetted into 4 ml cuvettes and the absorbance at 562 nm (25° C.) was monitored. After five minutes, 158 microliters of 10 mM gallium nitrate were added to the chelator, yielding a final gallium concentration of 0.5 mM. The increase in absorbance, due to formation of the ferrous iron-ferrozine complex, was measured for an additional fifteen minutes. The absorbance change as a function of time is shown in FIG. 4. The displacement curves of the free and immobilized deferoxamine are very similar. Somewhat surprisingly, there is no detectable change in metal binding, following conjugation of deferoxamine.

b. Competitive Binding of Iron By Free and Immobilized Deferoxamine

The relative iron binding affinities of deferoxamine and dextran-deferoxamine (DEX-DFO) were assessed by a competitive binding experiments. The iron radionuclide, $^{59}$Fe, was added to a mixture of the two chelators and the distribution of the chelated iron was determined by gel filtration chromatography, followed by liquid scintillation counting of the eluate fractions. In addition, the distribution of chelated iron was assayed 96 hours after the original determination, to see if any change had occurred.

Figure 5:
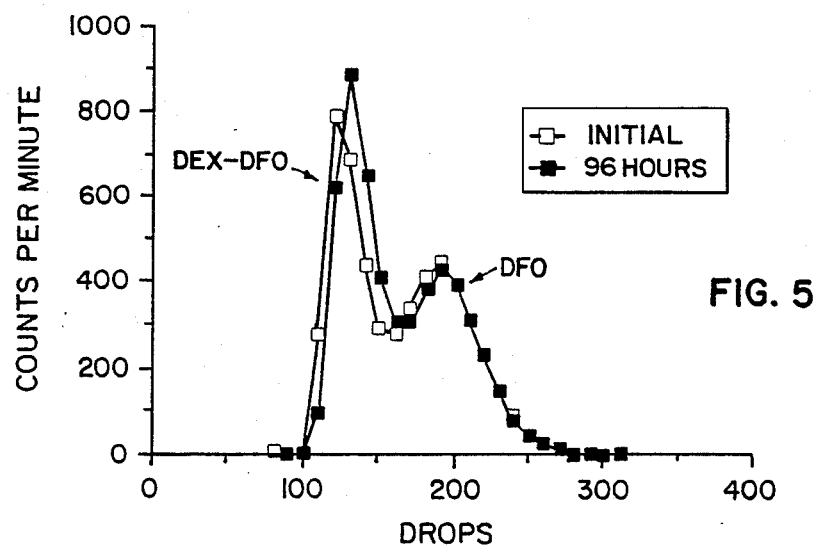
FIG. 5 is a graph showing the results of a competitive chelating study comparing deferoxamine and a deferoxamine-dextran adduct.

More specifically, a solution containing 0.05 mM deferoxamine and 0.05 mM dextran-deferoxamine (concentration based on deferoxamine equivalents) was prepared in 150 mM sodium chloride. This solution was filter sterilized with a 0.22 micron filter, to prevent bacterial growth during the 4 day incubation. A total of 20,000 cpm $^{59}$Fe (6 pmol) were added per milliliter of chelator mixture. Five hundred microliters of the solution were immediately chromatographed on a 1 ×12 cm Sephadex ® G-25 fine column equilibrated with 150 mM NaCl. The separations were mad at room temperature and 10 drop aliquots of the eluate collected. Each fraction was counted in 5 ml of counting fluid, in a Beckman LSI800 liquid scintillation counter. The original chelator/$^{59}$Fe solutions were allowed to stand at room temperature for 96 hours, followed by chromatography of a second 500 microliter aliquot. The eluate was collected and counted in the same manner as the initial sample. The resulting chromatograms for the initial distribution and for the sample after 4 days (96 hours) are summarized in FIG. 5.

Both chelators appear to bind the iron with approximately equal affinity. Significantly, there is no apparent net movement of iron from one chelator to the other, with time.

c. Comparison of In Vivo Activity of Free Deferoxamine and Dextran-Deferoxamine

Three, male, Swiss-Webster mice, each weighing approximately 35 grams, were used for this experiment. The mice were immobilized and then each was injected intravenously with 200 microliters of dextran-deferoxamine adduct, free deferoxamine, or dextran. Water was used as the diluent for all three compounds. Fifteen minutes after the first injection, each mouse had injected into the tail vein 200 microliters of 40 mM citrate buffer, pH 6.6, containing 338 microgram/ml of $^{59}$Fe. Each mouse was then placed in a separate metabolic cage. After 5 hours the urine and feces were collected, and the inside of the cages were each washed with 2 ml water. The wash was added to the collected waste, and the mixture was filtered through a coarse screen and brought to a total volume of ten ml. Five hundred microliters of each diluted waste were separately diluted with 10 ml of liquid scintillation fluid and counted. For each example, the net CPM excreted were as follows:

| Sample | Net CPM Recovered in Waste (excreted) |
|---|---|
| Dextran control | 4 |
| Free Deferoxamine | 352 |
| Dextran-deferoxamine | 255,680 |

Initially, each mouse received 1.64 $\times 10^6$ CPM. Therefore, the mouse that received the dextrandeferoxamine conjugate excreted 16% of the radioactive iron it received. The other two mice did not excrete any iron. A significant contributing factor to the different results from free deferoxamine and dextran deferoxamine is likely the increased vascular retention time observable for the adduct. That is, the free deferoxamine apparently failed to be retained in the vascular system sufficiently long to be effective under the test conditions. This difference, combined with a surprisingly low toxicity, makes the adduct desirable for a variety of clinical applications.

d. Removal of Ferric Ion From Solution With Deferoxamine Immobilized on Cellulose A stock solution of approximately 10 mM ferrous sulfate was made in distilled water. One hundred microliters of this solution were diluted to 7.0 ml. The solution was carefully mixed, and its concentration was measured by the ferrozine method. This method is commonly used for determinations of serum iron levels (see *Fundamentals of Clinical Chemistry*, Tietz, N. W. et al., W. B. Saunders, Philadelphia, 1976, incorporated herein by reference). The diluted stock solution was further diluted ten-fold. One ml of this solution was mixed with 1.0 ml reducing mixture and 100 microliters of a ferrozine stock was added. The concentration of the ferrozine stock was 7.0 mM. The ferrozine assay is suitable for measuring iron concentrations in the 1-50 micromolar range. The molar absorption coefficient of the complex between ferrous iron and ferrozine is 27,900 cm$^{-1}$ at 562 nm. The diluted iron solution yielded an absorbance of 0.170 at 562 nm, which relates to a concentration of 9.0 mM total iron in the stock solution. This stock was used as follows:

Several tubes containing one ml of wet, packed deferoxamine-derivatized cellulose were prepared. Varying amounts of the iron stock solution were added to yield final iron concentrations of 0, 32, 64, 128, 256 and 512 micromolar. A tube containing activated cellulose without immobilized deferoxamine was used as a control. The iron concentration in this latter tube was 128 micromolar. The tubes were allowed to mix on a rotator for several hours. Following this mixing, the deferoxamine-cellulose had acquired a yellow-orange color. The color intensity was greater in the tubes containing higher iron concentrations. The control cellulose remained white. Iron concentrations in the supernatants were measured, again using the ferrozine method.

After the cellulose had been allowed to sediment, aliquots of the supernatant were removed and any remaining cellulose "fines" were spun down in microfuge tubes. The following concentrations of iron were obtained for the seven tubes listed above: 0, 0, 0, 0, 23, 248 and 132 micromolar.

As expected, there was no iron in the "blank" tube. In the three tubes that originally contained 32, 64 and 128 micromolar iron, the metal ion was quantitatively removed. In the tube originally containing 256 micromolar iron approximately 90% was removed, and in the tube containing the highest iron concentration approximately 50% was removed. There was essentially no change in iron concentration in the tube containing underivatized cellulose.

These results also permit an estimate of total iron binding capacity in terms of maximal binding of iron. Based on the two highest iron concentrations one can estimate that approximately 1.4 micromoles can be bound per milliliter of wet deferoxamine modified cellulose. This corresponds to a binding capacity of 80 micrograms of free iron per milliliter of the wet packed cellulose (if made according to Example 7c).

EXAMPLE 11

Biological Activities of Deferoxamine Adducts

In past decades, biochemical researchers have investigated the deleterious effects of free or reactive iron, and recent experiments have examined its significance in biology and medicine. The results have suggested that iron, in conjunction with oxygen radicals, plays an important role in a number of different clinical situations, including myocardial infarct, shock, stroke, surgery and trauma. The data imply that the chelation or inactivation of iron may have considerable therapeutic potential, possibly due to the importance of iron as a redox catalyst in many harmful biochemical processes.

The only acceptable in vivo iron chelator, deferoxamine, has substantial therapeutic limitations due to its circulatory half-life and toxicity. An assortment of modified (immobilized) deferoxamine-based chelators are described above. Surprisingly, the immobilized forms of deferoxamine have a substantially longer in vivo half-life and a relatively low toxicity. Also, they have been demonstrated, in Examples above, to be effective iron chelators. The experiments reported below suggest that the immobilized deferoxamine compounds may be of significant use when iron-dependent pathophysiology is suspected in the etiology of a clinical condition.

A. Further Background

Ischemia can be either global or focal and is a component of shock, myocardial infarct, stroke, trauma and a number of other syndromes; see Freeman, B.A. et al., "Biology of Disease: Free Radicals and Oxygen Injury." *Lab Invest*, Vol. 47, p. 412–426 (1982); Bulkley, G. B., "The Role of Oxygen Free Radicals in Human Disease Processes.", *Surgery*, Vol. 94, p. 407–411 (1983); Slater, T. F. "Free Radical Mechanisms in Tissue Injury.", *Biochem J.*, Vol. 222, p. 1–15 (1984); Halliwell B., et al., "Oxygen Toxicity, Oxygen Radicals, Transition Metals and Disease.", *Biochem J.*, Vol. 219, p. 1–14 (1984); McCord, J. M., "Oxygen-Derived Free Radicals in Postischemic Tissue Injury.", *N. Eng. J. Med.*, Vol. 312, p. 159–163 (1985); and, Graf, E. et al., "Iron-Catalyzed Hydroxyl Radical Formation.", *J. Biol. Chem.*, Vol. 259, p. 3620–3624 (1984) the disclosures of which are incorporated herein by reference. Ischemia is perhaps most frequently encountered in emergency medicine. During tissue ischemia, blood flow is decreased or stopped, resulting in hypoxia and a number of physiological changes.

Ischemia is reversed when oxygenated blood flow returns to the hypoxic tissues (reperfusion), and a number of events occur. Xanthine oxidase and neutrophils are activated to produce superoxide and its dismutation product, hydrogen peroxide. The superoxide anion is capable of generating release of iron from ferritin; see, Thomas, C. D., et al, "Ferritin and Superoxide-Dependent Lipid Peroxidation.", *J. Biol.* Chem., Vol. 260, p. 3275–3280 (1985); and, Biemond, P., t al., "Superoxide-Dependent and -Independent Mechanisms of iron mobilization from ferritin by xanthine oxidase.", *Biochem J.*, Vol. 239, p. 169-173 (1986), the disclosures of which are incorporated by reference. This release of iron may cause problems; for example with the iron serving as a catalyst to oxidation/reduction reactions, which can lead to tissue damage.

b. Inhibition of Lipid Peroxidation By Immobilized Deferoxamine i. Murine Brain Homogenate Inhibition of lipid peroxidation was monitored in a murine brain homogenate system, using the method of Buege et al., to quantitate thiobarbituric reactive substances (TBARS), a general reflection of tissue damage including lipid peroxidation; see, Stocks J., et al., "Assay using Brain Homogenate For Measuring the Antioxident Activity of Biological Fluids.", Clin. Sci. Mol. Med., Vol. 47, p. 215-222 (1984); and Buege, J. A., et al., "Microsomal Lipid Peroxidation", Meth. Enzymol, Vol. 52, p. 320-310 (1978); the references being incorporated herein by reference.

A 25 g, male Swiss-Webster mouse was sacrificed, and the brain was carefully removed and washed in ice-cold deionized water. A 20% (w/v) homogenate was prepared by adding 2 ml buffer per 500 mg of brain, in an acid-washed Potter-Elvehjem homogenizer. Homogenization was carried out using eight strokes at high speed. Ferrous sulfate was added to the homogenate to give a final concentration of 10 micromolar.

Up to this point, all procedures were done on ice. Varying amounts of the chelators were then added to the homogenates and the tubes were gently rocked at room temperature for 30 minutes. A protein-free extract was prepared by addition of a strongly acidic solution of thiobarbituric acid (918 mM trichloroacetic acid, 25 mM thiobarbituric acid and 0.25 M HCl) followed by centrifugation at 1,000 $\times$ g for 10 minutes. The clear supernatant was heated in a boiling water bath for 15 minutes and was subsequently allowed to cool to room temperature. The absorbance of this solution was measured at 532 nm and the concentration of TBARS was calculated using a molar absorptivity of 1.56 $\times 10^5$ cm-1 (which corresponds to the absorbance maximum of the product formed between malonaldehyde and thiobarbituric acid). In a second experiment, human oxyhemoglobin was used at a final concentration of 500 micromolar in place of ferrous sulfate for driving lipid peroxidation. In all instances, the dextran-deferoxamine adduct was found to be just as effective as free deferoxamine in limiting lipid peroxidation.

Figure 6:
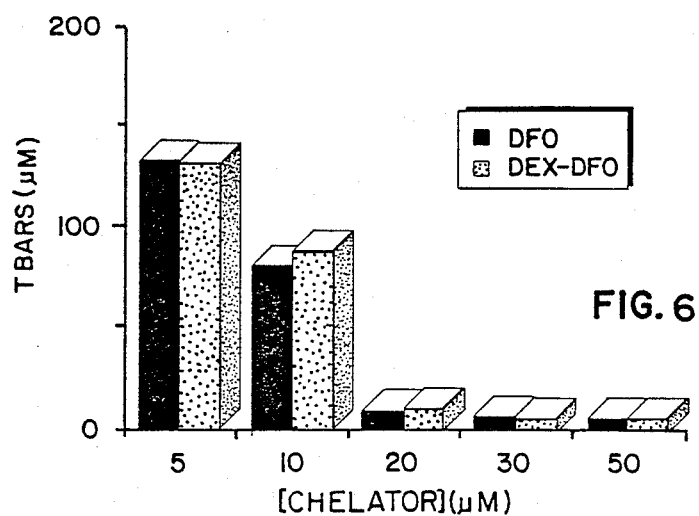
FIG. 6 is a graph reporting the results of experiments concerning inhibition of lipid peroxidation by deferoxamine and a dextran-deferoxamine adduct.
Figure 7:
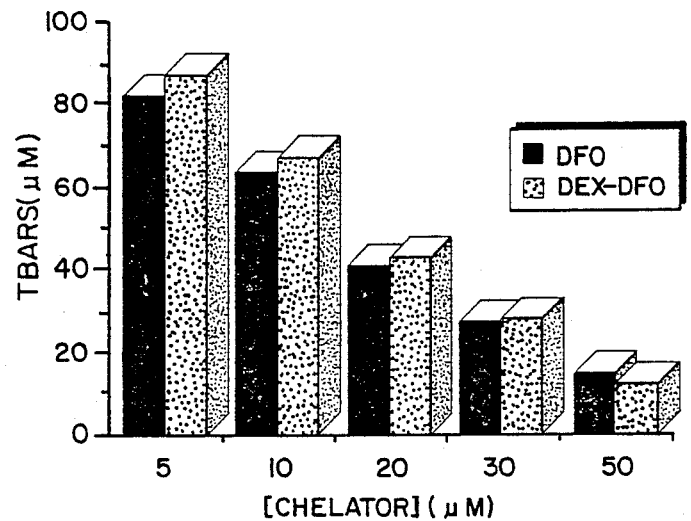
FIG. 7 is a graph reporting the comparative abilities of deferoxamine and a dextran-deferoxamine adduct to inhibit lipid peroxidation
Figure 8:
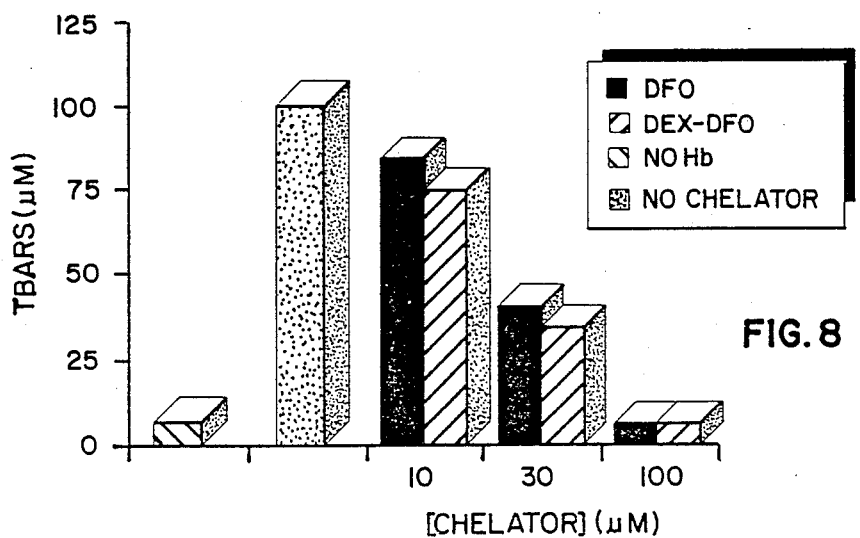
FIG. 8 is a graph reporting the results of an experiment concerning inhibition of lipid peroxidation by chelators according to the present invention.

The results are summarized in FIGS. 6, 7 and 8. In FIG. 6, inhibition is shown versus chelator concentration for a system including Tris buffer, pH 8.0, with 0.01 mM ferrous sulfate. For the experiment shown in FIG. 7, the solution contained isotonic saline and 0.01 mM ferrous sulfate. In FIG. 8, inhibition of hemoglobin mediated TBARS formation is shown; the first hemoglobin concentration being 0.5 mM. These results suggest that deferoxamine adducts will interrupt oxidation reactions of biological importance.

ii. Inhibition of Neutrophil-Mediated Erythrocyte Lysis By Immobilized Deferoxamine Human neutrophils (PMN), when activated, can destroy cells via an oxygen radical pathway. Free deferoxamine interferes with hemolysis of erythrocytes (RBC) by PMN. The protection against PMN-mediated red cell lysis afforded by deferoxamine and dextrandeferroxamine was compared. The experimental procedure followed was basically that of Vercellotti et al., J. Clin. Invest, Vol. 76, Sept. 1985, pp. 956-962 (1985); incorporated herein by reference.

Hemolysis was measured using a modification of the 51Cr release assay of Weiss; Weiss S. J., "The Role of Superoxide in the Destruction of Erythrocyte Targets by Human Neutrophils.", J. Biol. Chem., Vol. 255, p. 9912-9917 (1980), incorporated herein by reference. Isolation of PMN and RBC, and radiolabelling of RBC, were carried out as described by Vercellotti. The PMN (3.3 $\times 10^5$/ml) were incubated with the labelled RBC (3.3 $\times 10^6$/ml) in Hank's balanced salt solution containing 1% (w/v) gelatin. Chelator concentrations were either 0.1 mM or 1 mM in deferoxamine. The assays were carried out in microtest plates using a final volume of 0.3 ml. Phorbol myristate acetate (PMA) was added at a concentration of 10 mg/ml to activate the PMN and cell contact was achieved by centrifugation at 60 $\times$ g for 3 minutes. The test plates were then placed in a 37° C humidified atmosphere of 95% air/5% CO2 for 60 minutes. After incubation, the cells were centrifuged at 175 $\times$ g for 3 minutes; 0.15 ml of the supernatant were removed and radioactivity was determined by gamma counting.

Figure 9:
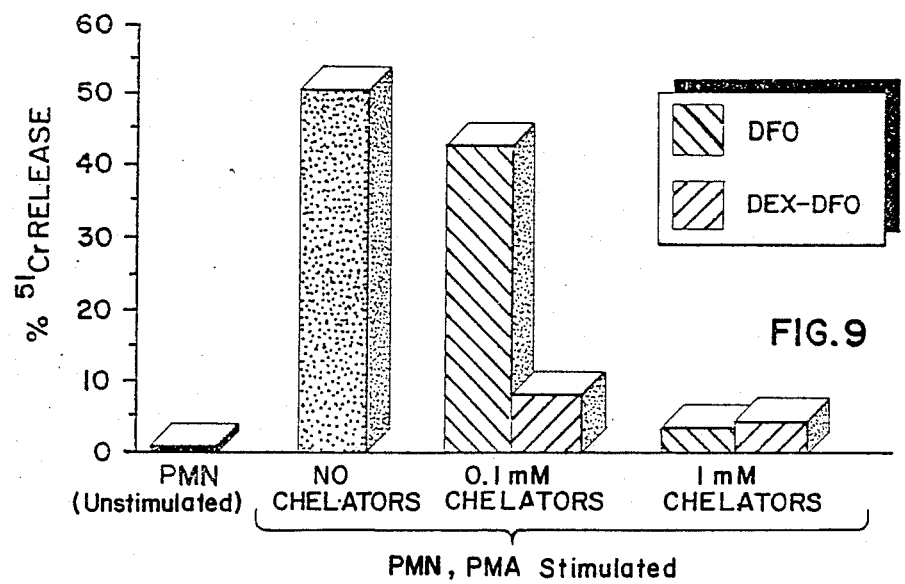
FIG. 9 is a graph depicting the results of an experiment comparing the abilities of deferoxamine and an adduct according to the present invention, to inhibit cell damage under certain circumstances.

The percent of $^{51}Cr$ released was calculated as follows: (Counts in the supernatant divided by total counts added per well) $\times 100$. Surprisingly, the immobilized deferoxamine afforded better protection against hemolysis than the free drug, at a concentration of 0.1 mM chelator (DFO equivalents). At the higher concentration of 1 mM, both compounds protected equally well. The results are summarized in FIG. 9.

EXAMPLE 12

In Vivo Efficacy of Deferoxamine and Conjugates Thereof In Renal Ischemia, In The Rat The model used for these studies is described in the literature; Paller, H. S. et al, "Oxygen free Radicals in Ischemic Acute Renal Failure in the Rat,"J. Clin. Invest. Vol. 74, p. 1156-1164 (1984), the disclosure of which is incorporated herein by reference.

Briefly, 60 minutes of ischemia were induced by clamping of the left renal artery in anesthesized animals (Sprague-Dauley male rats, 280-350 grams). The right kidney was removed. In these experiments, the treatment involved an infusion of the chelator, or control solution, initiated one minute before release of the renal artery clamp, and 59 minutes of reperfusion. A total dose of 50 mg/kg of chelator was used for free deferoxamine as well as the conjugate of inulin. The compounds were infused intravenously at a flow rate of 0.5 ml/min. The stock of the inulin-deferoxamine conjugate contained 100 mg/ml solid, of which 30 mg/ml was iron chelator. A control experiment using the polymer (inulin) was also conducted.

Two variables were assessed, serum creatinine and glomerular filtration rate (GFR). Values listed in Table I below are based on the average of four to seven animals in each group.

TABLE I

| Experiment | GFR (ml/min) | Serum Creatinine(mg %) |
|---|---|---|
| Deferoxamine (DFO) | .524 | 1.24 |
| DFO Inulin | .563 | 1.18 |
| Inulin Control | .220 | 2.97 |

The non-ischemic value for serum creatinine is 0.3-0.5 mg.% and the glomerular filtration rate is 1.0-1.2 ml/min for a rat with one kidney. The conclusion from these results is that the inulin adduct of DFO protects the ischemic kidney from reperfusion injury as effectively as the free drug. Free inulin had no protective effect.

A typical clinical use is suggested by the experiment and the underlying theory. Blood may be prevented from flowing to a tissue area during surgery or various other medical procedures, or during injury or the like. When blood flow is re-established to the tissue (reperfusion), tissue damage from oxidation reactions may result. The harmful oxidation may be inhibited by means inhibiting free iron from being available as a redox catalyst at or near the site of reperfusion. This may be accomplished through the utilization of an immobilized chelating agent according to the present invention. Generally, the immobilized chelating agent will be introduced in such a manner that it may flow into the injured site (site of ischemia) with the returning blood flow. In some instances, for example during surgery, it may be useful to provide the chelating agent to the site of ischemia both before and after reperfusion. This will be facilitated by using the immobilized chelators according to the present invention, which exhibit substantial vascular retention and low toxicity.

The invention has been described by reference to certain specific and preferred embodiments and techniques. However, it should be understood that many variations and modifications may be made while remaining within the spirit and scope of the invention.

What is claimed is:

1. A method for reducing the concentration of ferric ion or aluminum ion in the body fluid of a mammal comprising:
   administering to the mammal a covalently bonded adduct of deferoxamine and water-soluable inulin.

2. A method for reducing the concentration of ferric ion or aluminum ion in the body fluid of a mammal comprising:
   administering to the mammal a covalently bonded adduct of deferoxamine and water-soluable dextran.

3. A method for reducing the concentration of ferric ion or aluminum ion in the body fluid of a mammal comprising
   administering to the mammal a covalently bonded adduct of deferoxamine and water-soluable starch derivative.

4. A method for reducing the concentration of ferric ion or aluminum ion in the body fluid of a mammal comprising:
   administering to the mammal a covalently bonded adduct of deferoxamine and water-soluable hyaluronic acid.

5. A method according to claim 3 wherein the starch derivative is hydroxyethyl starch.

6. A method according to any of claims 1 through 5 wherein the administration is parenteral.

7. A method according to any of claims 1 through 5 wherein the administration is intravenous.

* * * * *

UNITED STATES PATENT AND TRADEMARK OFFICE
CERTIFICATE OF CORRECTION

PATENT NO. : 4,863,964

DATED : September 5, 1989

INVENTOR(S) : Hedlund et al.

It is certified that error appears in the above-identified patent and that said Letters Patent is hereby corrected as shown below:

At col. 2, line 68, for "carbobamoyl]" read --carbamoyl--.

At col. 4, line 35, for "plama" read --plasma--.

At col. 4, line 39, for "759-76" read --759-761--.

At. col. 4, line 43, for "intramuscularoor" read --intramuscular or--.

At col. 5, line 44, for "(500 ml" read --(500 ml)--.

At col. 5, line 67, for "6-0.7" read --0.6-0.7--.

At col. 7, lines 10-11, delete "incorporated herein by".

At col. 7, line 11, before "reference", insert --incorporated herein by--.

At col. 7, line 40, for "[.n" read --in--.

At col. 7, line 65, for "deteroxamine" read --deferoxamine--.

At col. 8, line 63, for "nM" read --mM--.

At col. 9, line 22, for "100 m" read --100ml--.

At col. 9, line 42, for "(0.09g)" read --(0.095g)--.

At col. 10, line 21, for "twelve" read --two--.

At col. 11, line 43, for "0.5M" read --0.25M--.

At col. 11, line 48, for "1.g" read --1.3g--.

UNITED STATES PATENT AND TRADEMARK OFFICE
CERTIFICATE OF CORRECTION

PATENT NO. : 4,863,964

DATED : September 5, 1989

INVENTOR(S) : Hedlund et al.

It is certified that error appears in the above-identified patent and that said Letters Patent is hereby corrected as shown below:

At col. 15, line 50, for "$M^{-12}cm-1$" read --$M^{-1}cm^{-1}$--.

At col. 19, line 39-40, for "105 cm-1" read --$10^5 cm^{-1}$--.

At col. 22, lines 6, 11, 17, and 23, for "soluable" read --soluble--.

At col. 22, line 15, after "comprising" insert the punctuation mark --:--.

Signed and Sealed this

Fifth Day of May, 1992

Attest:

DOUGLAS B. COMER

Attesting Officer

Acting Commissioner of Patents and Trademarks